(12) United States Patent
Manzo

(10) Patent No.: US 7,993,357 B2
(45) Date of Patent: Aug. 9, 2011

(54) METHOD AND APPARATUS FOR ANASTOMOSIS INCLUDING AN ANCHORING SLEEVE

(75) Inventor: Scott Manzo, Shelton, CT (US)

(73) Assignee: Tyco Healthcare Group, Norwalk, CT (US)

( * ) Notice: Subject to any disclaimer, the term of this patent is extended or adjusted under 35 U.S.C. 154(b) by 784 days.

(21) Appl. No.: 12/103,218

(22) Filed: Apr. 15, 2008

(65) Prior Publication Data
US 2008/0215063 A1    Sep. 4, 2008

Related U.S. Application Data

(63) Continuation of application No. 10/517,404, filed as application No. PCT/US03/011691 on Apr. 16, 2003, now Pat. No. 7,510,560.

(60) Provisional application No. 60/390,780, filed on Jun. 20, 2002.

(51) Int. Cl.
*A61B 17/08* (2006.01)

(52) U.S. Cl. ........................................ 606/153

(58) Field of Classification Search .................. 606/139, 606/142, 144, 148, 153, 198; 227/66, 67; 604/104–109
See application file for complete search history.

(56) References Cited

U.S. PATENT DOCUMENTS

| | | |
|---|---|---|
| 2,127,903 A | 8/1938 | Bowen |
| 3,713,447 A | 1/1973 | Adair |
| 4,553,543 A | 11/1985 | Amarasinghe |
| 4,608,965 A | 9/1986 | Anspach et al. |
| 4,803,984 A | 2/1989 | Narayanan et al. |
| 4,848,367 A | 7/1989 | Avant et al. |
| 4,911,164 A | 3/1990 | Roth |
| 4,957,499 A | 9/1990 | Lipatov et al. |
| 5,047,039 A | 9/1991 | Avant et al. |
| 5,122,156 A | 6/1992 | Granger et al. |
| 5,197,971 A | 3/1993 | Bonutti |
| 5,234,448 A | 8/1993 | Wholey et al. |
| 5,403,333 A | 4/1995 | Kaster et al. |
| 5,411,508 A | 5/1995 | Bessler et al. |
| 5,425,739 A | 6/1995 | Jessen |
| 5,464,414 A | 11/1995 | Cziffer |
| 5,464,415 A | 11/1995 | Chen |
| 5,478,353 A | 12/1995 | Yoon |
| 5,486,187 A | 1/1996 | Schenck |
| 5,540,701 A | 7/1996 | Sharkey et al. |

(Continued)

FOREIGN PATENT DOCUMENTS

WO    WO03/088848    10/2003

(Continued)

OTHER PUBLICATIONS

U.S. Appl. No. 10/514,140, entitled "Method and Apparatus for Radical Prostatectomy Anastomosis" filed Nov. 9, 2004.

(Continued)

*Primary Examiner* — Julian W Woo

(57) ABSTRACT

Apparatus for performing a surgical anastomosis include a tubular body having an onion portion formed near the distal end of the tubular body. The apparatus includes a sleeve having a radius sized and dimensioned to slidably receive the tubular body therein. The apparatus includes a plunger assembly sized and dimensioned to be slidably received within the central lumen of the tubular body. The plunger assembly includes a distal end configured and adapted to deploy the onion portion.

11 Claims, 7 Drawing Sheets

U.S. PATENT DOCUMENTS

| | | | |
|---|---|---|---|
| 5,545,171 A | 8/1996 | Sharkey et al. |
| 5,549,619 A | 8/1996 | Peters et al. |
| 5,554,162 A | 9/1996 | DeLange |
| 5,569,272 A | 10/1996 | Reed et al. |
| 5,578,044 A | 11/1996 | Gordon et al. |
| 5,591,179 A | 1/1997 | Edelstein |
| 5,591,206 A | 1/1997 | Moufarrège |
| 5,632,761 A | 5/1997 | Smith et al. |
| 5,695,504 A | 12/1997 | Gifford, III et al. |
| 5,700,272 A | 12/1997 | Gordon et al. |
| 5,702,412 A | 12/1997 | Popov et al. |
| 5,707,380 A | 1/1998 | Hinchliffe et al. |
| 5,713,889 A | 2/1998 | Chang |
| 5,716,370 A | 2/1998 | Williamson, IV et al. |
| 5,741,277 A | 4/1998 | Gordon et al. |
| 5,797,934 A | 8/1998 | Rygaard |
| 5,814,005 A | 9/1998 | Barra et al. |
| 5,817,113 A | 10/1998 | Gifford, III et al. |
| 5,833,698 A | 11/1998 | Hinchliffe et al. |
| 5,868,762 A | 2/1999 | Cragg et al. |
| 5,904,697 A | 5/1999 | Gifford, III et al. |
| 5,944,730 A | 8/1999 | Nobles et al. |
| 5,951,576 A | 9/1999 | Wakabayashi |
| 5,980,483 A | 11/1999 | Dimitri |
| 6,024,748 A | 2/2000 | Manzo et al. |
| 6,048,351 A | 4/2000 | Gordon et al. |
| 6,051,007 A | 4/2000 | Hogendijk et al. |
| 6,063,114 A | 5/2000 | Nash et al. |
| 6,080,167 A | 6/2000 | Lyell |
| 6,096,051 A | 8/2000 | Kortenbach et al. |
| 6,149,658 A | 11/2000 | Gardiner et al. |
| 6,152,937 A | 11/2000 | Peterson et al. |
| 6,171,319 B1 | 1/2001 | Nobles et al. |
| 6,171,321 B1 | 1/2001 | Gifford, III et al. |
| 6,176,864 B1 | 1/2001 | Chapman |
| 6,203,553 B1 | 3/2001 | Robertson et al. |
| 6,241,742 B1 | 6/2001 | Spence et al. |
| 6,245,083 B1 | 6/2001 | Black et al. |
| 6,254,617 B1 | 7/2001 | Spence et al. |
| 6,280,460 B1 | 8/2001 | Bolduc et al. |
| 7,175,660 B2 * | 2/2007 | Cartledge et al. ............. 606/139 |

FOREIGN PATENT DOCUMENTS

| | | |
|---|---|---|
| WO | WO04/000093 | 12/2003 |
| WO | WO04/000134 | 12/2003 |
| WO | WO04/000135 | 12/2003 |
| WO | WO04/000136 | 12/2003 |
| WO | WO2004/098418 | 11/2004 |

OTHER PUBLICATIONS

U.S. Appl. No. 10/516,437, entitled "Method and Apparatus for Anastomosis Including Annular Joining Member", filed Nov. 30, 2005.

U.S. Appl. No. 10/518,040, entitled "Method and Apparatus for Anastomosis Including Annular Adjoining Member", filed Dec. 9, 2004.

U.S. Appl. No. 10/514,774, entitled Method and Apparatus for Anastomosis Including an Anchoring Sleeve, filed Nov. 17, 2005.

U.S. Appl. No. 10/516,434, entitled "Method and Apparatus for Anastomosis", filed Nov. 30, 2004.

* cited by examiner

METHOD AND APPARATUS FOR ANASTOMOSIS INCLUDING AN ANCHORING SLEEVE

CROSS-REFERENCE TO RELATED APPLICATIONS

The present application is a Continuation Application claiming the benefit of and priority to U.S. application Ser. No. 10/517,404, filed on Dec. 7, 2004, which is a U.S. National Stage Application claiming the benefit of and priority to International Application Serial No. PCT/US2003/011691, filed on Apr. 16, 2003, which claims the benefit of and priority to U.S. Provisional Application Ser. No. 60/390,780, filed on Jun. 20, 2002, the entire content of each of which being incorporated herein by reference.

BACKGROUND

1. Technical Field

The present disclosure relates to apparatus and methods for joining tissue portions and, more particularly to anastomotic devices and methods for positioning and joining body vessels using an anchoring sleeve.

2. Background of Related Art

Anastomosis is the joining of two hollow or tubular structures. Certain body conduits are generally cylindrical in configuration and have a circular cross-section. When it is desired to suture such a conduit, typically for attachment to another body conduit, sutures are placed around the circumference of the conduit in order to maintain the patency of its lumen or channel. It can be appreciated that the sutures made on top of the conduit (i.e., on the side facing the surgeon) are made relatively more easily than the sutures made underneath the conduit (i.e., on the side facing away from the surgeon).

The complexity of joining two body vessels is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using prior art devices continues to be time consuming and requires great skill in order to be performed. Accordingly, the need exists for anastomosis devices which overcome the drawbacks of the prior art devices and which are quick and simple to use.

SUMMARY OF THE INVENTION

Apparatus and methods for performing a surgical anastomotic procedure are disclosed herein. Apparatus according to the present disclosure include a tubular body having a proximal end, a distal end and an onion portion formed near the distal end of the tubular body for engaging a first body vessel. The onion portion has a first position within a radial dimension of the tubular body and a second position outside the radial dimension of the tubular body. The apparatus includes a sleeve having an expandable cuff for engaging the second body vessel. The sleeve has a lumen for receiving the tubular body. The apparatus includes a plunger assembly for being recalled in the tubular body. The plunger assembly has a distal end arranged for deploying the onion portion from the first position to the second position.

Preferably, the tubular body has a first position in which the onion sleeve portion is substantially co-linear with or within the radial dimension of the tubular body and a second position in which the onion sleeve portion is deployed transversely with respect to the tubular body. The tubular body desirably has a radius and defines a central lumen having a radius.

In accordance with an embodiment of the present disclosure, the onion sleeve portion includes a plurality of longitudinally oriented slots defining a plurality of ribs. The ribs desirably include at least one flexure line. Preferably, each rib includes a distal flexure line, a proximal flexure line and an intermediate flexure line between the distal and proximal flexure lines. Most preferably, each intermediate flexure line is a double articulating joint. In is envisioned that the onion sleeve portion defines a radius about the intermediate flexure lines which is less than the radius of the tubular body.

In accordance with the present disclosure at least one of the plurality of ribs includes a barb extending therefrom for engaging the first body vessel. Preferably, each barb does not extend beyond the radius of the tubular body while the onion sleeve portion is in the first position. More preferably, each barb is formed on the rib at a location between the proximal flexure line and the intermediate flexure line. It is contemplated that each barb is oriented in a substantially proximal direction when the onion sleeve portion is in the second position.

In certain preferred embodiments, the onion portion has at least one expanded portion disposed outside the radial dimension of the tubular body when the onion portion is in the second position. The onion portion may have two expanded portions for engaging the first body vessel therebetween.

In accordance with an alternative embodiment of the present disclosure, it is envisioned that each rib of the onion sleeve portion includes a distal flexure line, a proximal flexure line, a pair of central flexure lines, a first intermediate flexure line between the distal the pair of central flexure lines and a second intermediate flexure line between the proximal flexure lines and the central flexure lines. Preferably, each first intermediate flexure line is a double articulating joint. More preferably, the onion sleeve portion defines a radius about the first intermediate flexure lines which is less than the radius of the tubular body.

It is envisioned that at least one of the plurality of ribs includes a barb extending therefrom, wherein each barb does not extend beyond the radius of the tubular body while the onion sleeve portion is in the first position. It is contemplated that each barb is formed on the rib at a location between the first intermediate flexure lines and the central flexure lines. Preferably, each barb is oriented in a substantially proximal direction when the onion sleeve portion is in the second position.

It is further contemplated that the head portion of the plunger assembly is provided with an engaging element configured and adapted to selectively couple with an engaging element provided at the distal end of the tubular body.

A preferred method of joining a first body vessel and a second body vessel comprises passing an apparatus through the second body vessel, the apparatus having an onion portion so that the onion portion is received in the first body vessel. The onion portion is deployed so that the onion portion moves to a position outside the radial dimension of the tubular body. The first body vessel and second body vessel are approximated and joined.

The method further includes the step of expanding an expandable cuff to engage the second body vessel. The apparatus may include a sleeve having the expandable cuff and the method may include moving the tubular body and the sleeve with respect to one another so as to approximate the first and second body vessels. The apparatus may have a plunger assembly for deploying the onion portion and the method may include advancing the plunger assembly so as to deploy the onion portion. The position of the tubular body and sleeve are desirably secured with respect to one another.

These and other features of the apparatus and method disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above and the detailed description of the embodiments given below, serve to explain the principles of the present disclosure.

DETAILED DESCRIPTION OF PREFERRED EMBODIMENTS

Figure 1:
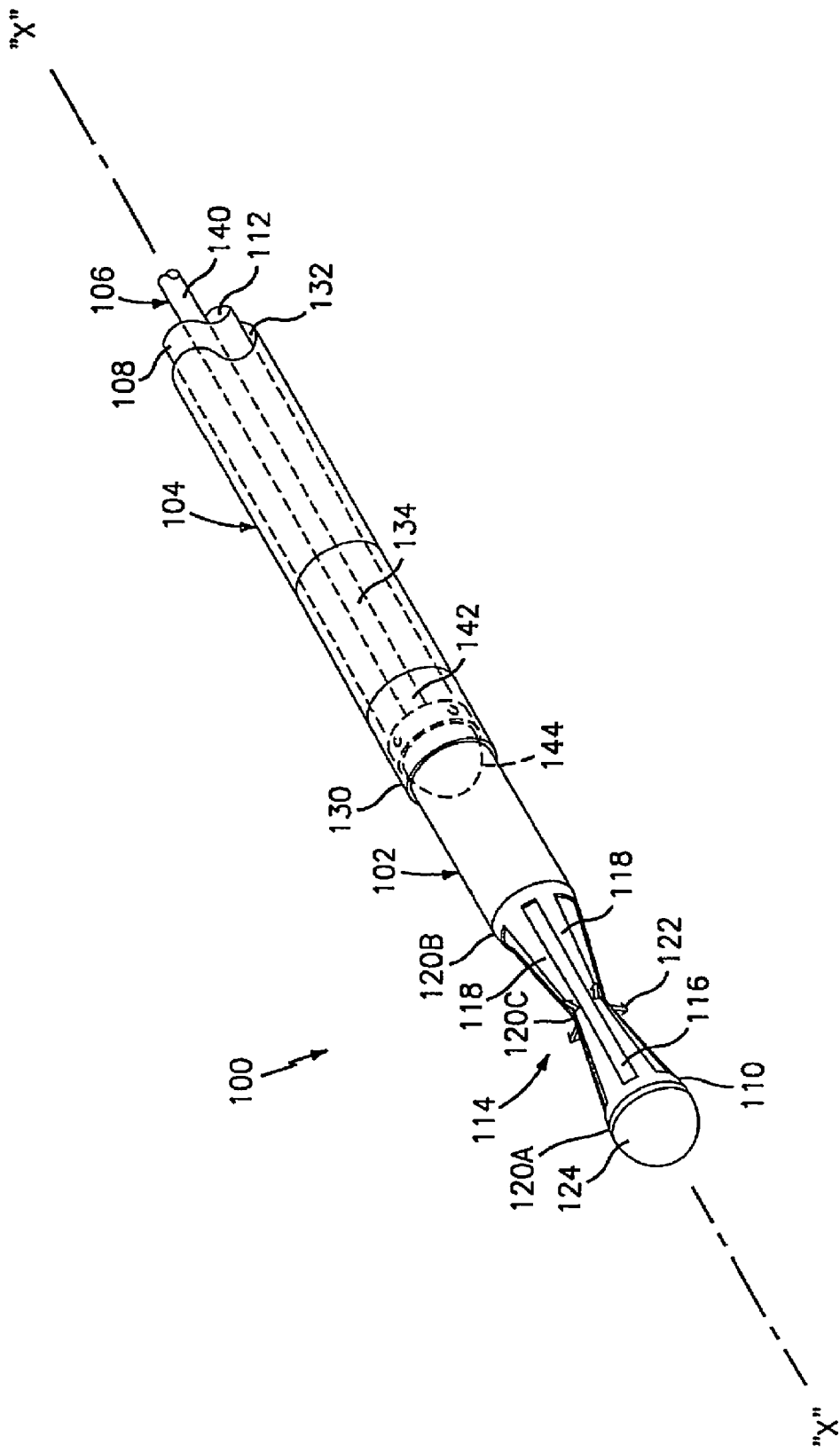
FIG. 1 is a perspective view of an anastomosis apparatus, in accordance to an embodiment of the present disclosure, shown in an insertion condition.

Preferred embodiments of the presently disclosed anastomosis apparatus will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Referring now to FIGS. 1-5, an anastomosis apparatus, in accordance with the principles of the present disclosure, is shown generally as reference numeral 100. Although apparatus 100 offers significant advantages to a radical prostatectomy procedure, it will be understood that the device is applicable for use in any anastomotic procedure where two body vessels are to be approximated and/or joined, including approximating and/or joining the urethra and bladder, intestinal portions of the body, blood vessels, and any other body vessels.

As seen in FIG. 1, apparatus 100 includes a tubular body 102, a sleeve 104 slidably received about tubular body 102 and a plunger assembly 106 slidably received within tubular body 102. Tubular body 102 includes a proximal end 108 and a distal end 110 and defines a central lumen 112 extending therethrough which central lumen 112 defines a central longitudinal axis "X".

Tubular body 102 includes an expandable anchor or onion sleeve portion 114 formed near distal end 110. In accordance with the present disclosure, onion sleeve portion 114 includes a plurality of radially formed, longitudinally oriented, elongated slots 116. Slots 116 define a plurality of longitudinally oriented ribs 118, each desirably having a plurality of transverse flexure lines 120 formed along the length thereof or being otherwise flexible. Preferably, ribs 118 include a distal and a proximal flexure line 120A, 120B, respectively, and an intermediate flexure line 120C. In one preferred embodiment, intermediate flexure line 120C is a double articulating flexure line, i.e., a flexure line which can be bent in two directions.

Figure 2:
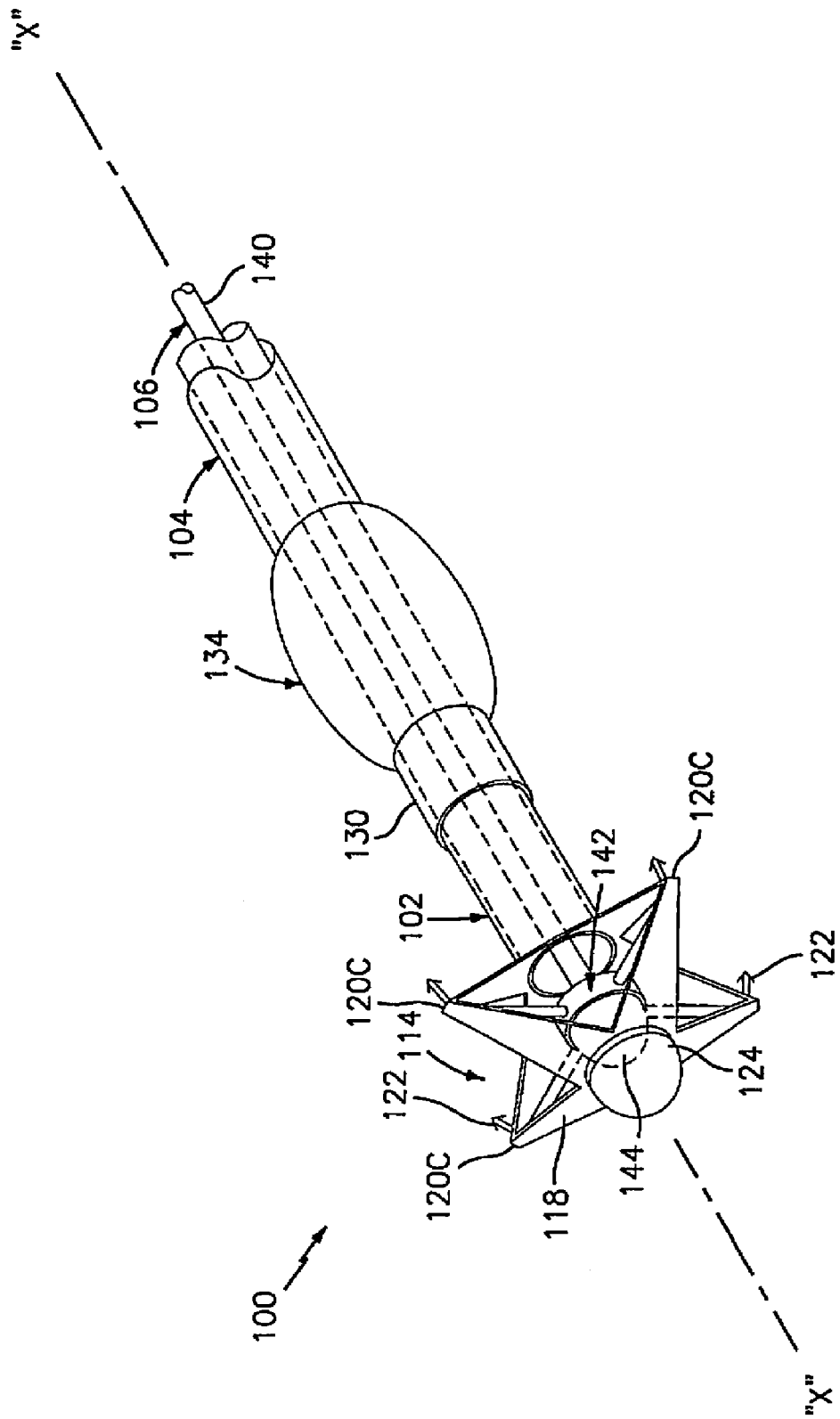
FIG. 2 is a perspective view of the anastomosis apparatus of FIG. 1, shown in a deployed condition.

In accordance with the present disclosure, onion sleeve portion 114 has a biased retracted position, as seen in FIG. 1, in which a radius of onion sleeve portion 114, about intermediate flexure lines 120C, is less than a radius of tubular body 102. Onion sleeve portion 114 has an unbiased expanded position, as seen in FIG. 2, in which the radius of onion sleeve 114, about intermediate flexure lines 120C, is greater than the radius of tubular body 102. In the embodiment shown, when onion sleeve portion 114 is in the expanded position, the portion of each rib 118 between intermediate flexure line 120C and proximal flexure line 120B is disposed at an angle with respect to the longitudinal "X" axis.

Onion sleeve portion 114 of tubular body 102 further desirably includes at least one barb 122 extending outwardly from each rib 118 and in a proximal direction. In accordance with the present disclosure, when onion sleeve portion 114 is in the retracted position, barbs 122 do not extend beyond the radial boundary of tubular sleeve 102. In this manner, barbs 122 do not interfere with the passage of tubular body 102 through sleeve 104. Further, in accordance with the present disclosure, when onion sleeve portion 114 is in the expanded position, it is preferred that barbs 122 are oriented substantially in a proximal direction and are substantially co-linear with the longitudinal "X" axis. While barbs 122 are preferred for penetrating body tissue, it is envisioned that the outer surface of rib 118 can be roughened in order to increase the gripping effect of rib 118 when in contact with body tissue.

It is contemplated that onion sleeve portion 114 and barbs 122 are made from a medical grade material, such as, for example, stainless steel or titanium, however, it is preferred that onion sleeve portion 114 and barbs 122 are made from a medical grade bio-absorbable material, such as, for example, polyglycolic acid (PGA) and/or polylactic acid (PLA).

As seen in the figures, distal end 110 of tubular body 102 is provided with a blunt end cap 124. However, tubular body 102 may have a distal end which opens into central lumen 112.

Sleeve 104 includes a distal end 130 and a proximal end (not shown) defining a lumen 132 extending therethrough. It is envisioned that distal end 130 of sleeve 104 can be tapered in order to facilitate passage of sleeve 104 through the body lumen. In accordance with the present disclosure, sleeve 104 includes an expandable cuff 134 provided near distal end 130 thereof. Preferably, expandable cuff 134 has a first position in which expandable cuff 134 has a radius which is less than or equal to a radius of sleeve 104 and a second position in which expandable cuff 134 has a radius which is greater than the radius of sleeve 104.

It is envisioned that sleeve 104 is provided with an inflation/deflation lumen (not shown) extending along the length thereof and which is in fluid communication with expandable cuff 134 through at least one access opening (not shown) formed in sleeve 104. In use, the inflation/deflation lumen is coupled to a source of inflation fluid (not shown) and a fluid is injected through the inflation/deflation lumen in order to inflate and expand cuff 134 to an expanded condition and thereby anchor or fix the placement of sleeve 104 within the body lumen. Concomitantly, withdrawal of the fluid used to inflate and expand cuff 134 will cause cuff 134 to deflate and thereby allow sleeve 104 to be withdrawn from the body lumen.

Expandable cuff 134 is preferably fabricated from a medical grade polymer having suitable flexibility and structural integrity to withstand the forces associated with the inflation of cuff 134 and with the function of anchoring sleeve 104 within the body lumen.

At least one annular seal, i.e., an O-ring, (not shown) is desirably provided between tubular body 102 and sleeve 104. The annular seal prevents or reduces the possibility of fluids from passing between tubular body 102 and sleeve 104.

Plunger assembly 106 includes a shaft 140 having a distal end 142, a proximal end (not shown) and a head portion 144 operatively coupled to distal end 142. In the embodiment shown, head portion 144 is preferably dimensioned to be received within central lumen 112 of tubular body 102. More preferably, head portion 144 defines a circular outer surface having an outer radius slightly smaller than the inner radius of tubular body 102

It is envisioned that the outer surface of head portion 144 is provided with a coupling element (not shown) configured and adapted to engage a corresponding coupling element (not shown) formed in either the inner surface of the distal end 110 of tubular body 102 or on the inner surface of end cap 124 of tubular body 102. It is contemplated that the coupling element formed on head portion 144 could be a helical thread which is configured and adapted to engage a corresponding helical thread formed on the inner surface of distal end 110 of the tubular body 102 at a location distal of onion sleeve portion 114. It is further contemplated that the coupling elements of head portion 144 and of distal end 110 of tubular body 102 may form a bayonet type coupling.

As will be described in greater detail below, in use, as plunger assembly 106 is distally advanced through central lumen 112 of tubular body 102, head portion 144 of plunger assembly 106 first engages the inner surface of ribs 118. As head portion 144 of plunger assembly 106 is further distally advanced, past onion sleeve portion 114, head portion 144 presses ribs 118 radially outward. In so doing, onion sleeve 114 goes from the biased retracted position to the unbiased expanded position, as discussed above. Head portion 144 is then further advanced until the coupling element of head portion 144 engages the coupling element formed at distal end 110 of tubular body 102.

It is envisioned that apparatus 100 be provided with a locking mechanism for securing tubular body 102 to sleeve 104 and to prevent their relative movement with respect to one another.

Figure 4:
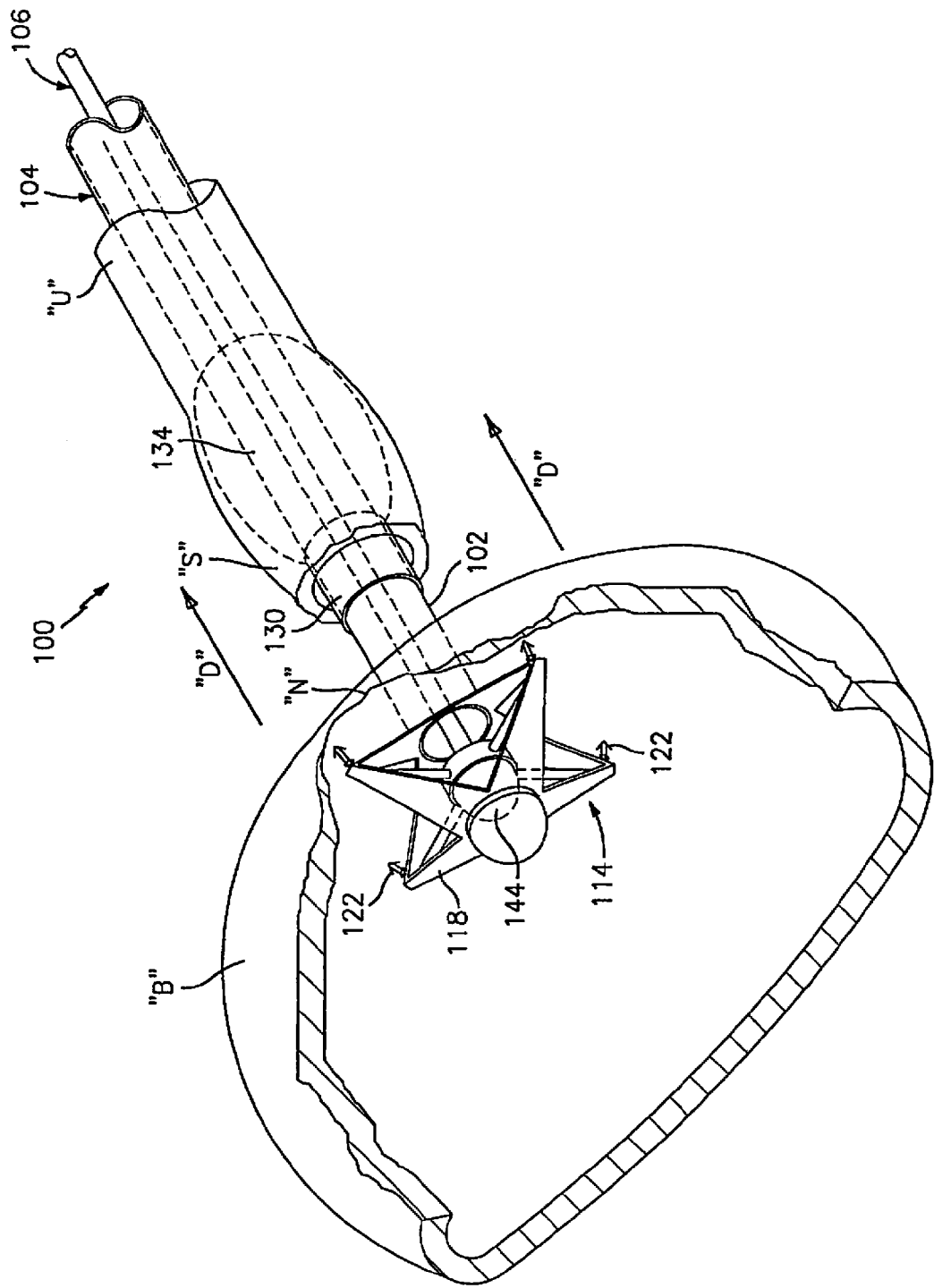
FIG. 4 is partial cross-sectional perspective view of the urinary system with the anastomosis apparatus of FIG. 1, with the radially expandable onion sleeve shown in a deployed condition within the hollow body organ and the radially expandable cuff shown in a deployed condition within the body lumen.
Figure 5:
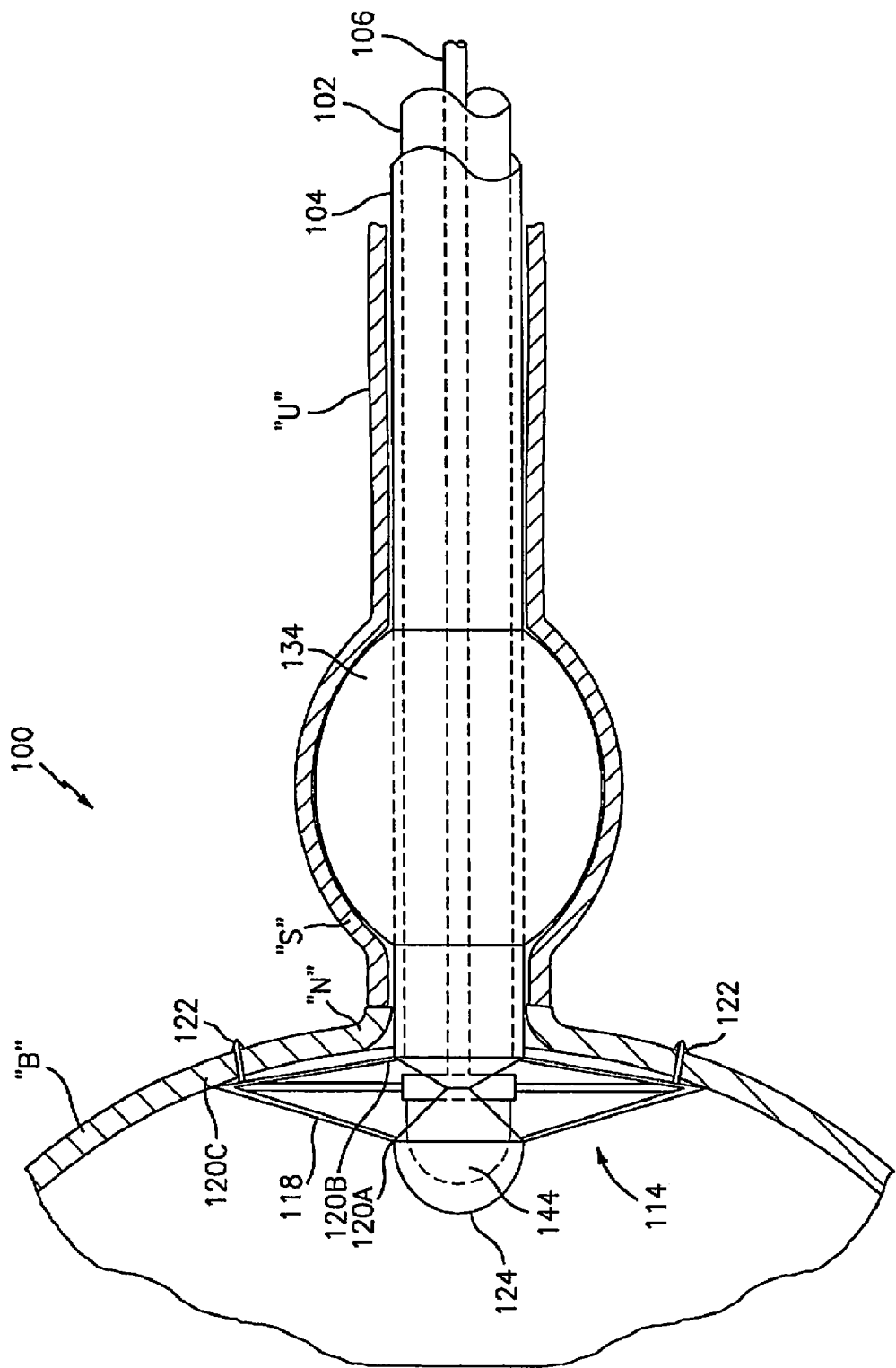
FIG. 5 is a cross-sectional side elevational view of the apparatus of FIG. 1, depicting the approximation of the hollow body organ to the body lumen.

A preferred method of use and operation of anastomosis apparatus 100 in a radical anastomotic procedure will now be described in greater detail with reference to FIGS. 1-5 and in particular with reference to FIGS. 3-5. Apparatus 100 can be used in either the retropubic or the perineal prostatectomy approaches. With the prostate removed, the bladder neck "N" of the bladder "B" is first reconstructed by evening the inner mucosal lining of bladder "B" and suturing it down to the outer wall of bladder "B" using known surgical techniques. Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate and retain distal end 108 of tubular body 102 within bladder "B" using a standard tennis racket type closure (i.e., the opening of the bladder neck constituting the head of the tennis racket and a radial incision extending from the bladder neck constituting the handle portion of the tennis racket. Most preferably, bladder neck "N" is sized to be approximately 7-8 mm in diameter.

Figure 3:
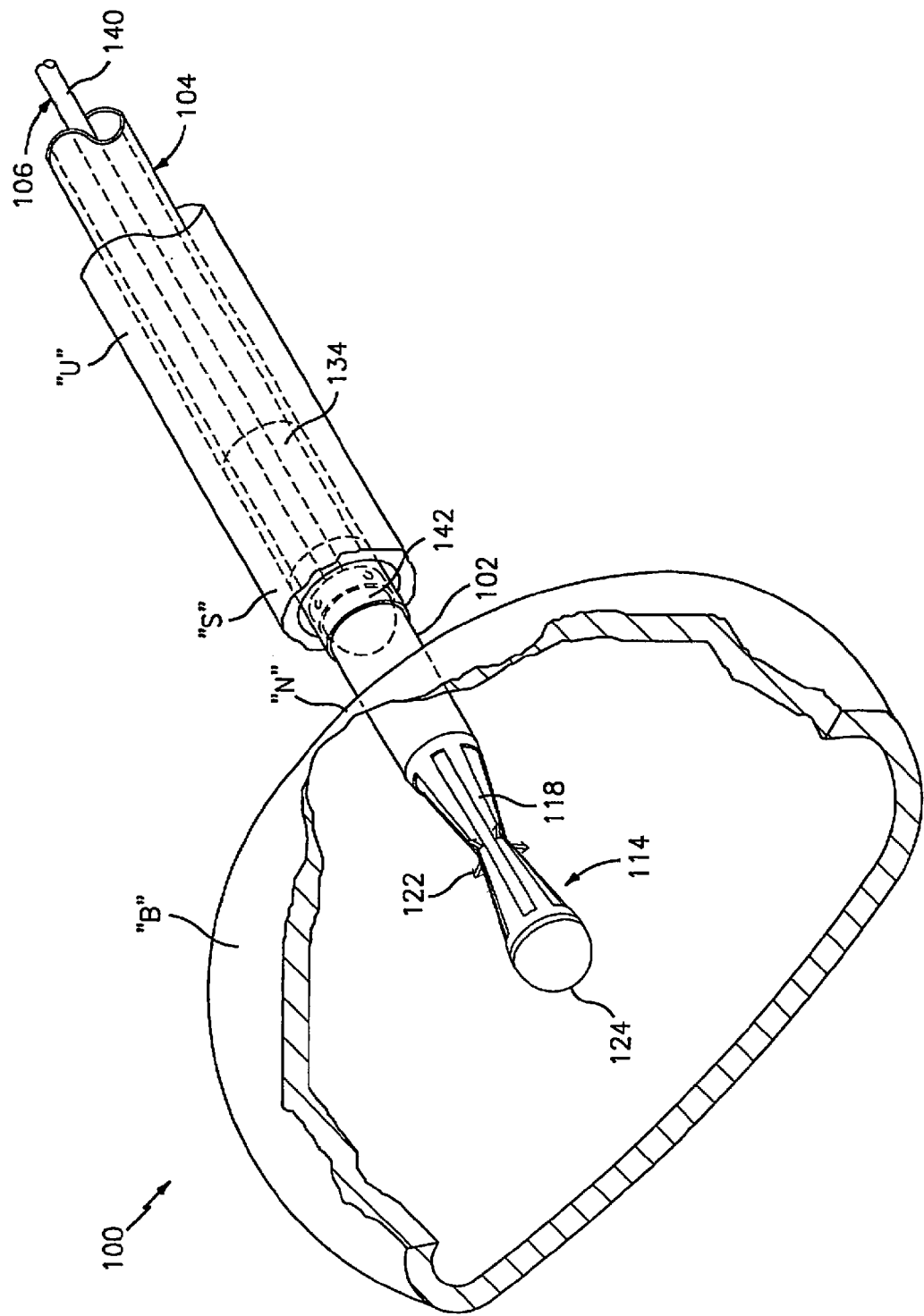
FIG. 3 is a partial cross-sectional perspective view of a portion of a urinary system with the anastomosis apparatus of FIG. 1, shown in the insertion condition, and illustrating the anastomosis apparatus being passed through a body lumen and entering a hollow body organ.

With bladder neck "N" reconstructed, apparatus 100, including tubular body 102 and sleeve 104, is passed transurethrally through urethra "U" until distal end 110 of tubular body 102 extends out of urethral stump "S" and into bladder "B" through bladder neck "N", as indicated by arrow "A" in FIG. 3. In particular, distal end 110 of tubular body 102 is preferably positioned such that expandable onion sleeve portion 114 of tubular body 102 is positioned entirely within bladder "B". In addition, distal end 130 of sleeve 104 is preferably positioned such that expandable cuff 134 is positioned near urethral stump "S" of urethra "U".

With tubular body 102 positioned within bladder "B", plunger assembly 106 is distally advanced through central lumen 112 of tubular body 102. As described above, as plunger assembly 106 is distally advanced through central lumen 112 of tubular body 102, head portion 144 of plunger assembly 106 first engages the inner surface of ribs 118. As head portion 144 of plunger assembly 106 is further distally advanced, past onion sleeve portion 114, head portion 144 presses ribs 118 radially outward. In so doing, onion sleeve portion 114 is deployed from the biased retracted position to the unbiased expanded position. As such, barbs 122 of ribs 118 of onion sleeve portion 114 become oriented in a substantially proximal direction. Head portion 144 is then further advanced until the coupling element of head portion 144 engages the coupling element formed at distal end 110 of tubular body 102.

With head portion 144 of plunger assembly 106 coupled to distal end 110 of tubular body 102 and onion sleeve portion 114 in the expanded position, either plunger assembly 106 or both plunger assembly 106 and tubular body 102 are pulled in a proximal direction through urethra "U" as indicated by arrows "D". By pulling at least tubular body 102 in a proximal direction, barbs 122 of onion sleeve portion 114 are driven into the wall of bladder "B".

With sleeve 104 positioned near urethral stump "S", a fluid (i.e., air, carbon dioxide, saline or the like) is introduced into cuff 134 to thereby expand and inflate cuff 134. Inflation of cuff 134 results in the radial expansion of cuff 134 and in turn the pressing of cuff 134 against the inner surface of urethra "U", thus preventing axial movement of sleeve 104 through urethra with onion sleeve portion 114 of tubular body 102 anchored in bladder "B" and cuff 134 of sleeve 104 secured within urethra "U", either tubular body 102, plunger assembly 106 or both tubular body 102 and plunger assembly 106 are withdrawn in a proximal direction through sleeve 104 in order to approximate bladder "B" to urethra "U". Once bladder "B" has been approximated into contact with urethra "U", tubular body 102 is locked in position with respect to sleeve 104 thereby maintaining bladder "B" approximated with urethra "U". The body 102 may be fixed in relation to sleeve 104 using a latch, or any other known means.

With tubular body 102 fixed in position with respect to sleeve 104, head portion 144 of plunger assembly 106 is disengaged from distal end 110 of tubular body 102 and plunger assembly 106 is withdrawn therefrom. It is envisioned that, with plunger assembly 106 removed from central lumen 112 of tubular body 102, that tubular body 102 and sleeve 104 act like a Foley-type catheter to create a passage, defined by slots 116 and central lumen 112, through which body fluid (i.e., urine) is permitted to pass from bladder "B" and out through urethra "U".

In accordance with the present disclosure, it is preferred that tubular body 102 and sleeve 104 are maintained within bladder "B" and urethra "U" for a period of several weeks or for a period of time sufficient for bladder neck "N" and urethral stump "S" to heal and "grow" together. Once bladder neck "N" and urethral stump "S" have sufficiently healed, and barbs 122 sufficiently dissolved and absorbed within the body, onion sleeve portion 114 and cuff 134 are retracted and tubular body 102 and sleeve 104 are withdrawn from urethra "U".

The expandable anchor for engaging the first and/or second body vessel may comprise any expandable structure, including those disclosed in certain embodiments of the following PCT applications, all filed on an even date herewith: Application Entitled Method And Apparatus For Anastomosis Including An Anchoring Sleeve, invented by Scott Manzo; Method And Apparatus For Anastomosis Including An Anchoring Sleeve, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Anchor, invented by Russell Heinrich and Scott Manzo (Ref. No. 2798); the disclosures of which are all hereby incorporated by reference herein, in their entirety.

The joining member for joining the first and/or second body vessel may comprise any joining member, including those disclosed in certain embodiments of the following PCT Applications: Method And Apparatus For Anastomosis Including An Anchoring Sleeve, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Anchor For Engaging A Body Vessel And Deployable Sutures, invented by Scott Manzo; Method And Apparatus For Anastomosis Including An Anchor For Engaging A Body Vessel And Deployable Sutures, invented by Scott Manzo; Method And Apparatus For Anastomosis Including An Expandable Member, invented by Russell Heinrich and Scott Manzo; Method And Apparatus For Anastomosis Including An Expandable Anchor, invented by Russell Heinrich and Scott Manzo; the disclosures of which are all hereby incorporated by reference herein, in their entirety.

Figure 7:
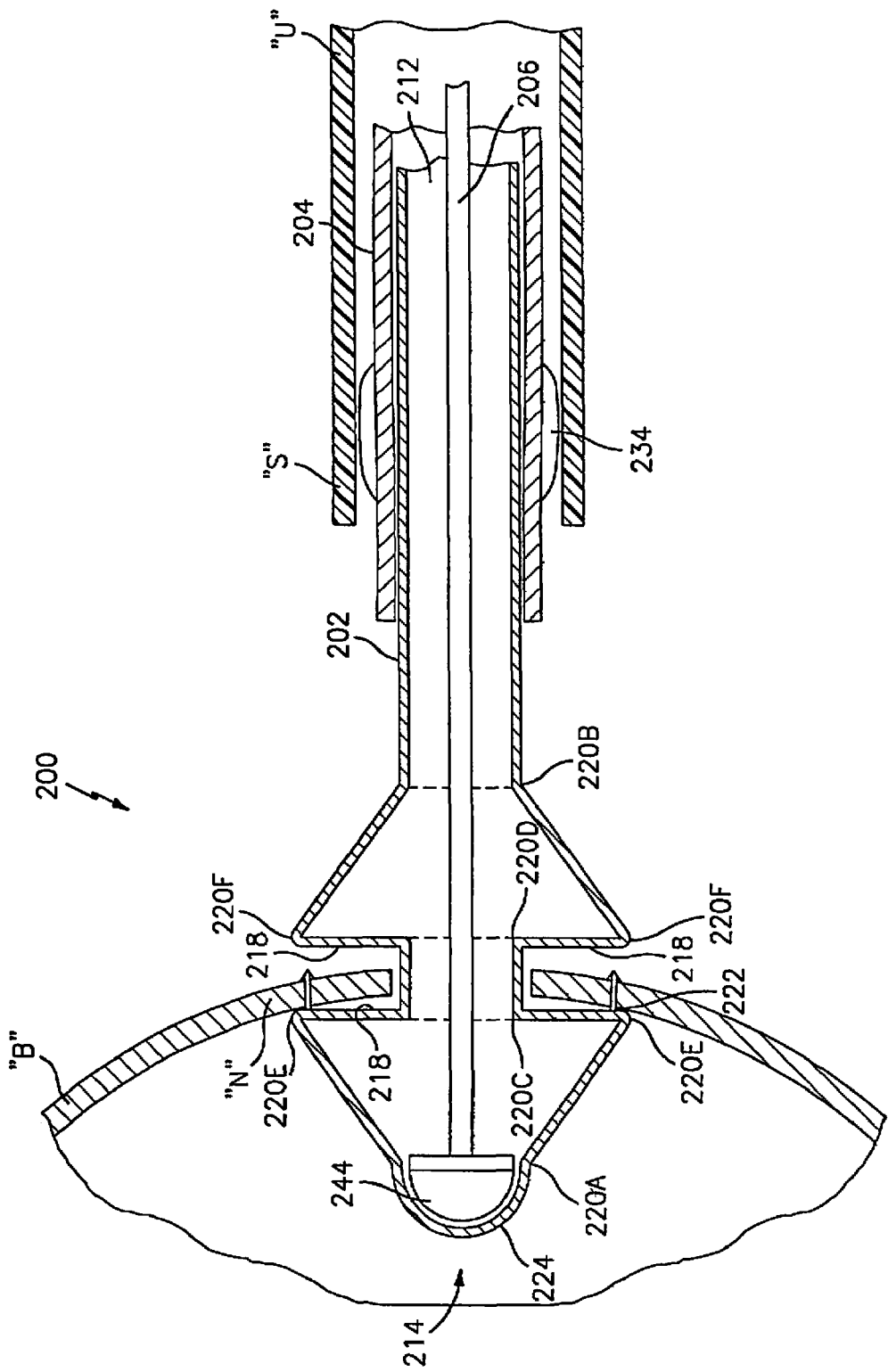
FIG. 7 is a cross-sectional side elevational view of the anastomosis apparatus of FIG. 6, depicting the approximation of the hollow body organ to the body lumen.

Turning now to FIGS. 7 and 8, an anastomosis apparatus, in accordance with an alternative embodiment of the disclosure, is shown generally as reference numeral 200. Apparatus 200 includes a tubular body 202, a sleeve 204 slidably received about tubular body 202 and a plunger assembly 206 slidably received within tubular body 202. Tubular body 202 includes a distal end 210 and a proximal end (not shown) and defines a central lumen 212 extending therethrough which central lumen 212 defines a central longitudinal axis "X".

Tubular body 202 includes an expandable onion sleeve portion 214 formed near distal end 210. In accordance with the present disclosure, onion sleeve portion 214 includes a plurality of radially formed, longitudinally oriented, elongated slots 216. Slots 216 define a plurality of longitudinally oriented ribs 218, each having a plurality of transverse flexure lines 220 formed along the length thereof. Preferably, each rib 218 includes a distal flexure line 220A, a proximal flexure line 220B, a pair of central flexure lines 220C, 220D, a first intermediate flexure line 220E formed between distal flexure line 220A and central flexure line 220C and a second intermediate flexure line 220F formed between proximal flexure line 220B and central flexure line 220D.

Figure 6:
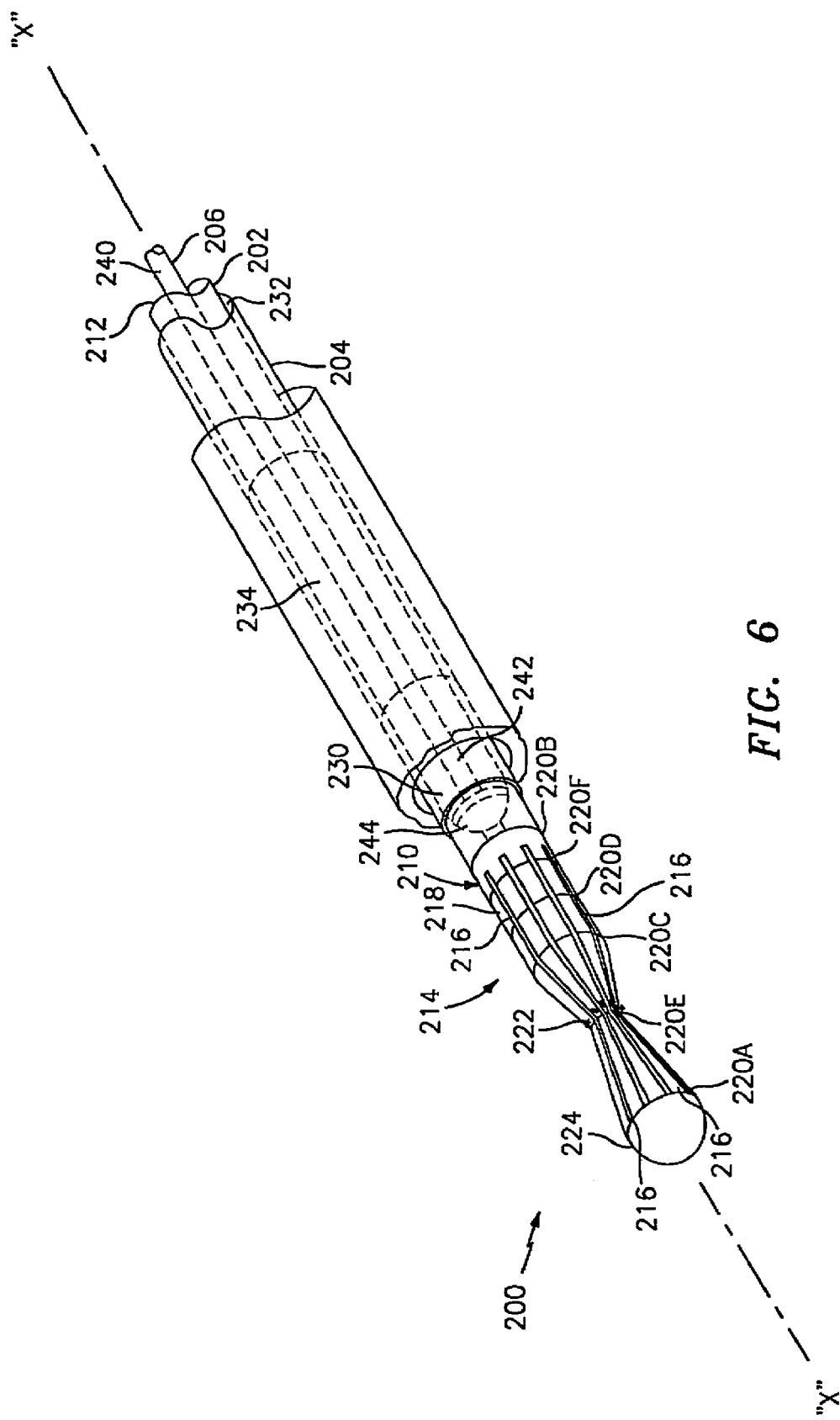
FIG. 6 is a perspective view of an anastomosis apparatus, in accordance to another embodiment of the present disclosure, shown in an insertion condition.

In accordance with the present disclosure, flexure lines 220A-220F are configured and adapted such that onion sleeve portion 214 has a retracted position, as seen in FIG. 6, in which a radius of onion sleeve portion 214, about first intermediate flexure lines 220E, is less than a radius of tubular body 202. Onion sleeve portion 214 has an unbiased position, as seen in FIG. 7, in which the radius of onion sleeve 214, about intermediate flexure lines 220E, is greater than the radius of the tubular body 202. Preferably, when onion sleeve portion 214 is in the expanded position, the portion of each rib 218 between first intermediate flexure line 220E and central flexure line 220C is orthogonal with respect to the longitudinal "X" axis. Further, when onion sleeve portion 214 is in the expanded position, the portion of each rib 218 between second intermediate flexure 220F and central flexure line 220D is orthogonal with respect to the longitudinal "X" axis.

Onion sleeve portion 214 of tubular body 202 further includes at least one barb 222 extending outwardly from each rib 218. Preferably, the at least one barb 222 is provided on the portion of rib 218 between first intermediate flexure line 220E and central flexure line 220C. Preferably, first intermediate flexure line 220E is a double articulating flexure line. Accordingly, when onion sleeve portion 214 is in the retracted position, barbs 222 do not extend beyond the radial boundary of tubular sleeve 202. In this manner, barbs 222 do not interfere with the passage of tubular body 202 through sleeve 204. Further, in accordance with the present disclosure, when onion sleeve portion 214 is in the expanded position, it is preferred that barbs 222 are oriented substantially in a proximal direction and are substantially parallel with the longitudinal "X" axis.

As seen in FIGS. 6 and 7, distal end 210 of tubular body 202 is provided with a blunt end cap 224. However, it is envisioned that tubular body 202 can have a distal end 210 which opens into central lumen 212.

Sleeve 204 includes a distal end 230 and a proximal end (not shown) defining a lumen 232 extending therethrough. It is envisioned that distal end 230 of sleeve 204 can be tapered in order to facilitate passage of sleeve 204 through the body lumen. In accordance with the present disclosure, sleeve 204 includes an expandable cuff 234 provided near distal end 230 thereof. Preferably, expandable cuff 234 has a first position in which expandable cuff 234 has a radius which is less than or equal to a radius of sleeve 204 and a second position in which expandable cuff 234 has a radius which is greater than the radius of sleeve 204.

It is envisioned that sleeve 204 is provided with an inflation/deflation lumen (not shown) extending along the length thereof and which is in fluid communication with expandable cuff 234 through at least one access opening (not shown) formed in sleeve 204. In use, the inflation/deflation lumen is coupled to a source of inflation fluid (not shown) and a fluid is injected through the inflation/deflation lumen in order to inflate and expand cuff 234 to an expanded condition and thereby anchor or fix the placement of sleeve 204 within the body lumen. Concomitantly, withdrawal of the fluid used to inflate and expand cuff 234 will cause cuff 234 to deflate and thereby allow sleeve 204 to be withdrawn from the body lumen.

It is contemplated that at least one annular seal, i.e., an O-ring, (not shown) may be provided between tubular body 202 and sleeve 204. Accordingly, it is envisioned that the annular seal prevents or reduces the possibility of fluids from passing between tubular body 202 and sleeve 204.

Plunger assembly 206 includes a shaft 240 having a distal end 242, a proximal end (not shown) and a head portion 244 operatively coupled to distal end 242. In accordance with the present disclosure, head portion 244 is preferably dimensioned to be received within central lumen 212 of tubular body 202. More preferably, head portion 244 defines a circular outer surface having an outer radius slightly smaller than the inner radius of tubular body 202

It is envisioned that the outer surface of head portion 244 is provided with a coupling element, similar to coupling element of head portion 144, configured and adapted to engage a corresponding coupling element formed in either the inner surface of the distal end 210 of tubular body 202 or on the inner surface of end cap 224 of tubular body 202.

In use, as plunger assembly 206 is distally advanced through central lumen 212 of tubular body 202, head portion 244 of plunger assembly 206 first engages the inner surface of ribs 218. As head portion 244 of plunger assembly 206 is further distally advanced, past onion sleeve portion 214, head portion 244 presses ribs 218 radially outward. In so doing, onion sleeve 214 goes from the biased retracted position to the unbiased expanded position, as discussed above. Head portion 244 is then further advanced until the coupling element of head portion 244 engages the coupling element formed at distal end 210 of tubular body 202. In other embodiments, other means are used to deploy the onion sleeve portion.

It is envisioned that apparatus 200 be provided with a locking mechanism for securing tubular body 202 to sleeve 204 and to prevent their relative movement with respect to one another. The body 202 and sleeve 204 may be secured using latch or any other means.

With bladder neck "N" reconstructed, apparatus 200, including tubular body 202 and sleeve 204, is passed transurethrally through urethra "U" until distal end 210 of tubular body 202 extends out of urethral stump "S" and into bladder "B" through bladder neck "N". In particular, distal end 210 of tubular body 202 is preferably positioned such that first intermediate flexure line 220E is positioned distally of bladder neck "N" and second intermediate flexure line 220F is positioned proximally of bladder neck "N". In addition, distal end 230 of sleeve 204 is preferably positioned such that expandable cuff 234 is positioned near urethral stump "S" of urethra "U".

With tubular body 202 so positioned with respect to bladder neck "N", plunger assembly 206 is distally advanced through central lumen 212 of tubular body 202. As described above, as plunger assembly 206 is distally advanced through central lumen 212 of tubular body 202, head portion 244 of plunger assembly 206 first engages the inner surface of ribs 218, in particular, the inner surface of ribs 218 disposed between first intermediate flexure line 220E and central flexure line 220C. As head portion 244 of plunger assembly 206 is further distally advanced, past onion sleeve portion 214, head portion 244 presses ribs 118 radially outward. In so doing, onion sleeve portion 214 is deployed from the retracted position to the expanded position. As such, barbs 222 of ribs 218 of onion sleeve portion 214 become oriented in a substantially proximal direction. Head portion 244 is then further advanced until the coupling element of head portion 244 engages the coupling element formed at distal end 210 of tubular body 202.

With head portion 244 of plunger assembly 206 coupled to distal end 210 of tubular body 202 and onion sleeve portion 214 in the expanded position, shaft 240 of plunger assembly 206 is pulled in a proximal direction through tubular body 202, while holding tubular body 202 in a fixed position. By pulling shaft 240 in a proximal direction and holding tubular body 202 in a fixed position, second intermediate flexure line 220F of onion sleeve portion 214 is expanded radially outward.

With barbs 222 oriented in a proximal direction, as shaft 240 is pulled in a proximal direction, onion sleeve portion 214, being a double onion, acts like a clamp to close down about bladder neck "N". In so doing, barbs 222 are driven through bladder neck "N" while rib 218, between central flexure line 220D and second intermediate flexure line 220F, acts to support the exterior surface of bladder neck "N". It is envisioned that the portion of each rib 218, between central flexure line 220D and second intermediate flexure line 220F, is provided with an opening for accommodating passage of barbs 222 therethrough during the clamping process. With barbs 222 anchored in the wall of bladder neck "N", shaft 240 of plunger assembly 206 is moved in a proximal direction, with respect to tubular body 202, in order to return second intermediate flexure line 220F to the retracted position.

With sleeve 204 positioned near urethral stump "S", a fluid is introduced into cuff 234 to thereby expand and inflate cuff 234. Inflation of cuff 234 results in the radial expansion of cuff 234 and in turn the pressing of cuff 234 against the inner surface of urethra "U", thus preventing axial movement of sleeve 204 through urethra "U".

With onion sleeve portion 214 of tubular body 202 anchored in bladder "B" and cuff 234 of sleeve 204 secured within urethra "U", either tubular body 202, plunger assembly 206 or both tubular body 202 and plunger assembly 206 are withdrawn in a proximal direction through sleeve 204 in order to approximate bladder "B" to urethra "U". Once bladder "B" has been approximated into contact with urethra "U", tubular body 202 is locked in position with respect to sleeve 204 thereby maintaining bladder "B" approximated with urethra "U".

With tubular body 202 fixed in position with respect to sleeve 204, head portion 244 of plunger assembly 206 is disengaged from distal end 210 of tubular body 202 and plunger assembly 206 is withdrawn therefrom. In accordance with the present disclosure, it is preferred that tubular body 202 and sleeve 204 are maintained within bladder "B" and urethra "U" for a period of several weeks or for a period of time sufficient for bladder neck "N" and urethral stump "S" to heal and "grow" together. Once bladder neck "N" and urethral stump "S" have sufficiently healed, and barbs 222 sufficiently dissolved and absorbed within the body, onion sleeve portion 214 and cuff 234 are retracted and tubular body 202 and sleeve 204 withdrawn from urethra "U".

While apparatus in accordance with the present disclosure have been described as being used in connection with radical prostatectomy procedures, it is envisioned that apparatus having similar structures and modes of operation can be used in various other surgical procedures. It will be understood that various modifications may be made to the embodiments of the presently disclosed anastomosis devices and methods disclosed herein. For example, the onion sleeve portion may be deployable by other means. One end of the ribs may be attached to a sleeve that is moved proximally, bending the ribs outwardly. In other embodiments, the body has arms that are deployed outwardly by the head portion of the plunger assembly or by some other means. Therefore, the above description should not be construed as limiting, but merely as an exemplification of a preferred embodiment. Those skilled in the art will envision other modifications within the scope of the present disclosure.

What is claimed is:

1. An apparatus for joining a first body vessel and a second body vessel, comprising:
    a) a tubular body having a proximal end, a distal end, and an expandable anchor formed near the distal end of the tubular body for engaging the first body vessel, the expandable anchor having a first position within a radial dimension of the tubular body and a second position outside the radial dimension of the tubular body, the expandable anchor having a plurality of barbs for engaging the first body vessel, the barbs being arranged to face in a proximal direction when the expandable anchor is in the second position; and
    b) a sleeve having an expandable cuff for engaging the second body vessel, the sleeve having a lumen for receiving the tubular body.

2. The apparatus according to claim 1, further comprising a plunger assembly received in the tubular body, the plunger assembly having a distal end arranged for selectively engaging an interior surface of the expandable anchor to deploy the expandable anchor from the first position to the second position.

3. The apparatus according to claim 2, wherein the plunger assembly comprises a head portion longitudinally movable relative to the tubular body to selectively engage the interior surface of the expandable anchor, the head portion dimensioned to press radially outward on the interior surface of the expandable anchor to deploy the expandable anchor from the first position to the second position.

4. The apparatus according to claim 3, wherein the head portion comprises a coupling element configured to selectively engage a corresponding coupling element formed near the distal end of the tubular body.

5. The apparatus according to claim 4, wherein the coupling element of the head portion and the coupling element formed near the distal end of the tubular body comprise corresponding helical threads.

6. The apparatus according to claim 4, wherein the coupling element of the head portion and the coupling element formed near the distal end of the tubular body comprise corresponding a bayonet type coupling.

7. The apparatus according to claim 2, wherein the plunger assembly is longitudinally movable relative to the tubular body to selectively approximate the first body vessel and the second body vessel when the expandable anchor is in the second position.

8. The apparatus according to claim 1, wherein the expandable anchor comprises an onion portion of the tubular body, the onion portion comprising a plurality of ribs defining a plurality of longitudinally oriented slots.

9. The apparatus according to claim 8, wherein each of the ribs has at least one flexure line defined therein.

10. An apparatus for joining a first body vessel and a second body vessel, comprising:

a) a tubular body having a proximal end, a distal end, and an expandable anchor formed near the distal end of the tubular body for engaging the first body vessel, the expandable anchor defining an over-center mechanism having a retracted position within a radial dimension of the tubular body and an expanded position outside the radial dimension of the tubular body;

b) a sleeve having an expandable cuff for engaging the second body vessel, the sleeve having a lumen for receiving the tubular body; and c) a plunger assembly received in the tubular body, the plunger assembly having a distal end arranged to selectively advance distally past the expandable anchor to deploy the expandable anchor from the retracted position to the expanded position.

11. The apparatus according to claim 10, wherein the expandable anchor is biased when in the retracted position and unbiased when in the expanded position.

* * * * *